United States Patent [19]
Imran

[11] Patent Number: 5,415,166
[45] Date of Patent: * May 16, 1995

[54] ENDOCARDIAL MAPPING APPARATUS AND CYLINDRICAL SEMICONDUCTOR DEVICE MOUNTING STRUCTURE FOR USE THEREWITH AND METHOD

[75] Inventor: Mir A. Imran, Palo Alto, Calif.

[73] Assignee: Cardiac Pathways Corporation, Sunnyvale, Calif.

[*] Notice: The portion of the term of this patent subsequent to Oct. 20, 2009 has been disclaimed.

[21] Appl. No.: 127,699

[22] Filed: Sep. 28, 1993

Related U.S. Application Data

[63] Continuation-in-part of Ser. No. 919,198, Jul. 24, 1992, Pat. No. 5,279,299, which is a continuation of Ser. No. 656,764, Feb. 15, 1991, Pat. No. 5,156,151.

[51] Int. Cl.[6] .......................... A61B 5/04; A61N 1/05
[52] U.S. Cl. ..................................... 128/642; 607/122
[58] Field of Search ............... 128/642; 607/115, 116, 607/122, 123, 125–128

[56] References Cited

U.S. PATENT DOCUMENTS 4,649,924  3/1987  Taccardi .
4,699,147 10/1987  Chilson et al. .
5,156,151 10/1992  Imran ................................ 128/642

FOREIGN PATENT DOCUMENTS 2552035  5/1977  Germany ........................... 128/642

Primary Examiner—Lee S. Cohen
Assistant Examiner—Jeffrey R. Jastrzab
Attorney, Agent, or Firm—Flehr, Hohbach, Test, Albritton & Herbert

[57] ABSTRACT

An apparatus for mapping the wall of a chamber of the heart. The apparatus includes a flexible elongate tubular member having proximal and distal extremities and at least one lumen extending therethrough. A plurality of longitudinally and radially spaced-apart electrodes are provided. An expandable device is carried by the distal extremity of the flexible elongate tubular member and is movable between a contracted position and an expanded position. The electrodes are mounted on the expandable device so that when the expandable device is moved to its expanded position in the chamber of the heart the electrodes are moved into engagement with the wall forming the chamber of the heart. Leads for conducting electrical energy are in contact with the electrodes and extend into the flexible elongate tubular member. An electrical apparatus is connected to the leads for performing electrical functions with respect to the electrodes and includes at least one semiconductor device carried by the distal extremity of the flexible elongate tubular member in close proximity to the expandable device.

15 Claims, 3 Drawing Sheets

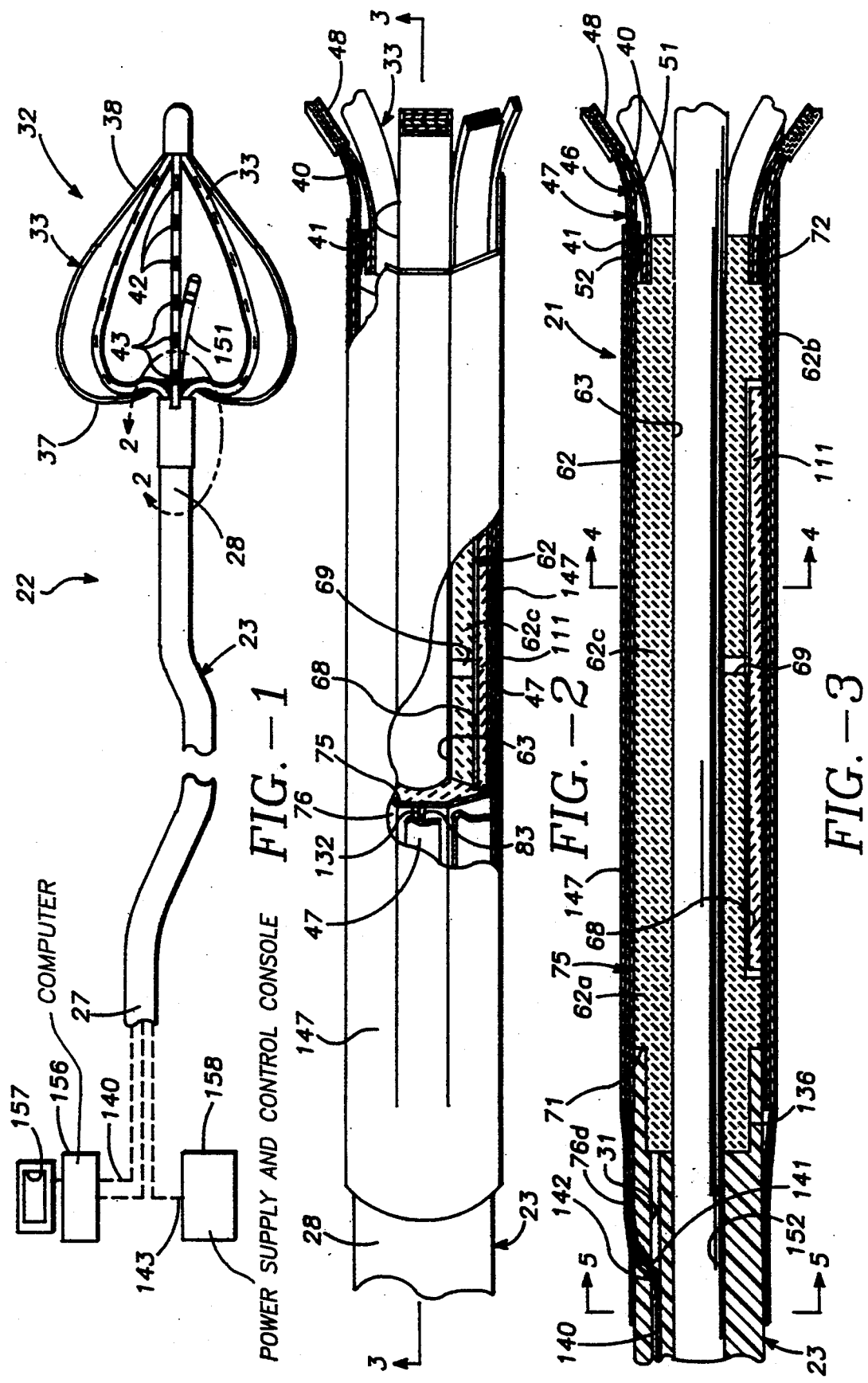

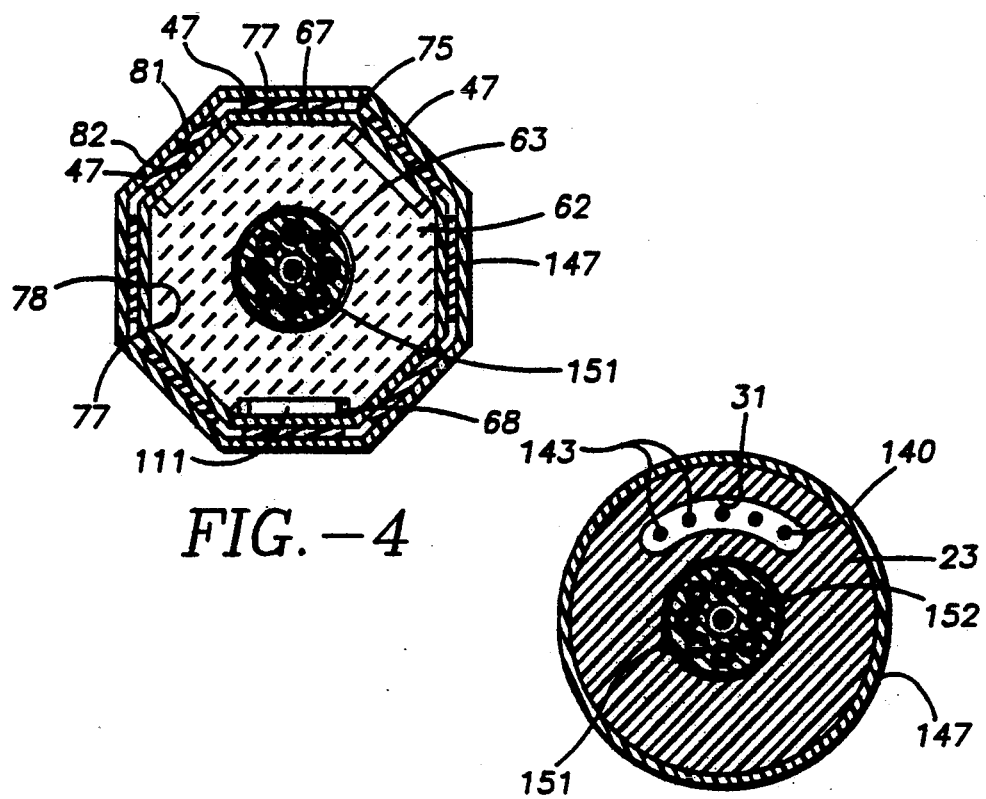
FIG.-4
FIG.-5
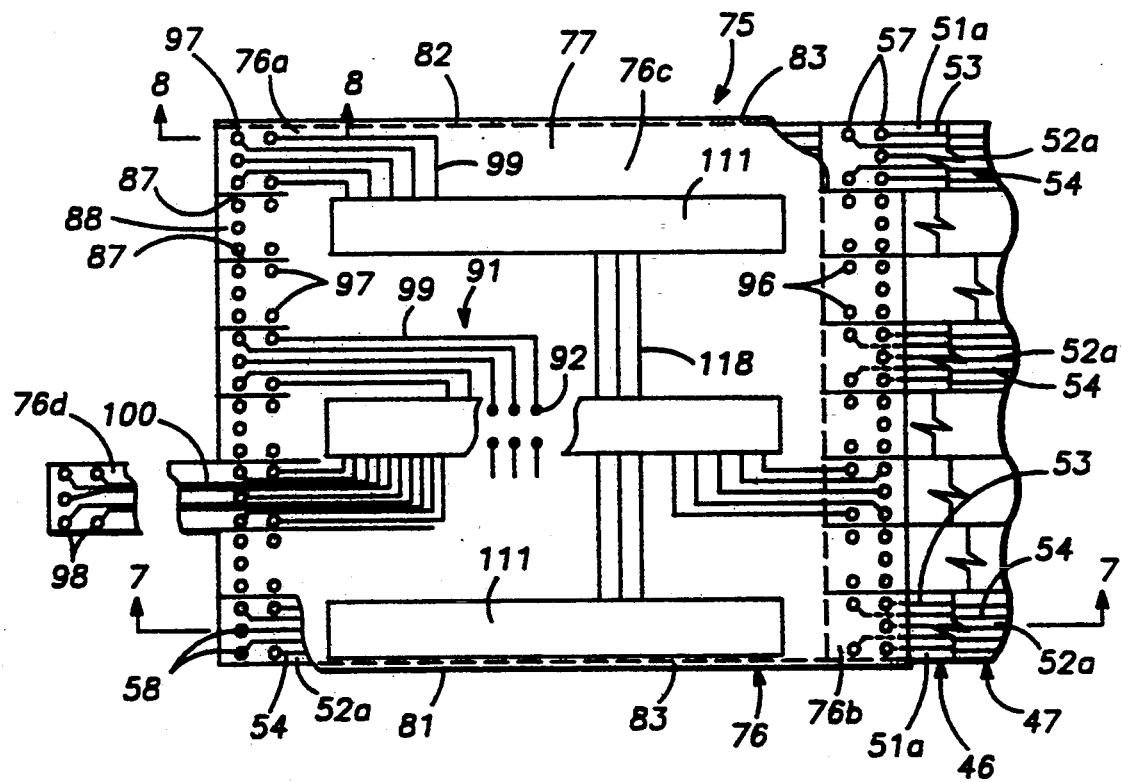
FIG.-6

ENDOCARDIAL MAPPING APPARATUS AND CYLINDRICAL SEMICONDUCTOR DEVICE MOUNTING STRUCTURE FOR USE THEREWITH AND METHOD

CROSS-REFERENCE TO RELATED APPLICATIONS

This application is a continuation-in-part of application Ser. No. 07/919,198 filed Jul. 24, 1992, now U.S. Pat. No. 5,279,299 which is a continuation of application Ser. No. 07/656,764 filed Feb. 15, 1991, now U.S. Pat. No. 5,156,151.

BACKGROUND OF THE INVENTION

1. Field of the Invention

This invention relates to a mounting structure for use with semiconductor devices and, more specifically, to a mounting structure for use with semiconductor devices at the distal extremity of a medical apparatus.

2. Description of the Related Art

Catheters have been provided with flexible members having probes on the distal end for introduction into the human heart. The probes have electrodes mounted thereon for performing endocardial mapping. In general, these catheters and probes can have only a limited number of electrodes because, among other things, of the limited space available in the flexible member to accommodate conducting wires for carrying the electronic signals from the mapping electrodes. Because of the foregoing, there is a need for a new and improved endocardial mapping apparatus which overcomes the above named disadvantages.

OBJECTS OF THE INVENTION

In general, it is an object of the present invention to provide an endocardial mapping apparatus which utilizes a significant number of electrodes.

Another object of the invention is to provide an apparatus of the above character in which a semiconductor device with multiplexers is provided on the distal extremity of the apparatus.

Another object of the invention is to provide an apparatus of the above character in which the semiconductor device is carried by a cylindrical mounting structure with interconnect pads spaced around the proximal and distal end portions thereof.

Another object of the invention is to provide a cylindrical mounting structure of the above character which utilizes a flex circuit having an interconnect pad on one side thereof which is electrically accessible from the other side without the necessity of an electroplated feed-through hole.

Another object of the invention is to provide a method by which a flex circuit is initially secured by negative pressure to a mandrel while forming the cylindrical mounting structure.

Additional objects and features of the invention will appear from the following description from which the preferred embodiments are set forth in detail in conjunction with the accompanying drawings.

BRIEF DESCRIPTION OF THE DRAWINGS

FIG. 1 is a perspective view of a medical apparatus having a distally carried cylindrical mounting structure of the present invention.

FIG. 2 is an enlarged view, partially cut away, taken along the line 2—2 of the distal extremity of the medical apparatus shown in FIG. 1.

FIG. 3 is a cross-sectional view taken along the line 3—3 of FIG. 1.

FIG. 4 is a cross-sectional view taken along the line 4—4 of FIG. 3.

FIG. 5 is a cross-sectional view taken along the line 5—5 of FIG. 3.

FIG. 6 is an enlarged view, partially cut away, of the partially assembled cylindrical mounting structure of the present invention.

SUMMARY OF THE INVENTION

Figure 7:
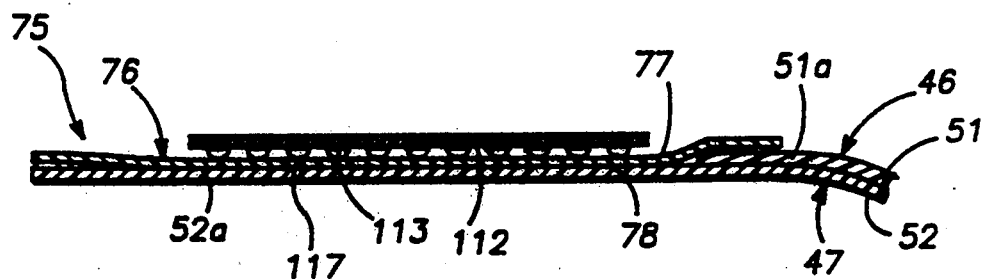
FIG. 7 is a cross-sectional view taken along the line 7—7 of FIG. 6.

In general, an apparatus for mapping the wall of a chamber of the heart is provided which includes a flexible elongate tubular member having proximal and distal extremities and at least one lumen extending therethrough. A plurality of longitudinally and radially spaced-apart electrodes are provided. Expandable means is carried by the distal extremity of the flexible elongate tubular member and is movable between a contracted position and an expanded position. Means is included in the apparatus for mounting the electrodes on the expandable means so that when the expandable means is moved to its expanded position in the chamber of the heart the electrodes are moved into engagement with the wall forming the chamber of the heart. Lead means for conducting electrical energy are in contact with the electrodes and extend into the flexible elongate tubular member. Electrical means is connected to the lead means for performing electrical functions with respect to the electrodes and includes a semiconductor device carried by the distal extremity of the flexible elongate tubular member in close proximity to the expandable means.

DETAILED DESCRIPTION

More particularly, cylindrical mounting structure 21 of the present invention can be adapted for use with a medical device or apparatus 22 for mapping the wall of a chamber of the heart. A suitable apparatus is described in detail in copending patent application Ser. No. 07/919,198 filed Jul. 24, 1992, now U.S. Pat. No. 5,279,299. Briefly, apparatus 22 has a flexible elongate tubular member 23 formed of a suitable material such as plastic which is circular in cross-section and is provided with proximal and distal extremities 27 and 28 (see FIG. 1). Tubular member 23 is provided with at least one lumen 31 extending therethrough from proximal extremity 27 to distal extremity 28 and carries a probe device in the form of basket assembly 32 at distal extremity 28 thereof for insertion into a body of a human.

Basket assembly 32 serves as expandable means carried by distal extremity 28 of tubular member 23 and is movable between a contracted position and an expanded position. Basket assembly 32 is provided with a plurality of and as shown in the drawings eight radially and circumferentially spaced-apart longitudinally-extending flexible arms 33 having joined proximal and distal extremities or end portions 37 and 38. Elongate flexible arms 33 have an outwardly bowed shaped memory and are each provided with a metal strip 40 which is included within the means for providing the desired shape to basket assembly 32. Metal strips 40 extend longitudinally between proximal and distal extremities 37 and 38 to impart springiness to elongate flexible arms 33 and are interconnected at their proximal ends by a ring 41. The ends of metal strips 40 are circumferentially spaced around the inside of ring 41 and joined thereto by any suitable means such as spot welding.

A plurality of longitudinally spaced-apart first and second electrodes 42 and 43 are carried by each elongate flexible arm 33 for engaging the wall of the heart. Although only a limited number of electrodes 42 and 43 have been shown, it should be appreciated that a significant number of electrodes, as for example at least twenty, can be carried by basket assembly 32 and be within the scope of the present invention. Elongate flexible arms 33 include at least first and second juxtaposed flex circuits 46 and 47 which are secured to respective metal strips 40 by a tube or sheath 48 made from any suitable insulating heat shrinkable material such as plastic and shrunk thereon by the application of heat. Flex circuits 46 and 47 are formed from respective first and second plastic strips 51 and 52 made from a suitable material such as polyimide having a thickness ranging from 0.0010 to 0.0015 inches (See FIGS. 3 and 6). Strips 51 and 52 have respective first and second proximal strip or end portions 51a and 52a.

Each of first and second strips 51 and 52 has a layer of a suitable conductive material such as copper disposed thereon by either additive or subtractive techniques known to those skilled in the art to form spaced-apart electrodes 42 and 43 and a respective plurality of first leads 53 extending from first electrodes 42 and second leads 54 extending from second electrodes 43 to respective first and second proximal strip portions 51a and 52a. First leads 53 electrically connect first electrodes 42 on first flex circuit 46 to first interconnect pads 57 formed from the copper conductive material on first proximal strip portion 51a. Second leads 53 electrically connect second electrodes 43 on second flex circuit 47 to second interconnect pads 58 formed from the copper conductive material on second proximal strip portion 52a. For simplicity, leads 53 and 54 are shown only on several of strip portions 51a and 52a in FIG. 6. First leads 53 and second leads 54 are included within the respective first and second lead means of apparatus 22 for conducting electrical energy in contact with electrodes 42 and 43 to proximal extremities 37 of elongate flexible arms 33. First and second interconnect pads 57 and 58 are arranged in similar patterns on respective first and second proximal strip portions 51a and 52a and are provided with solder bumps 59 thereon. Sheath 48 is included within the means for mounting electrodes 42 and 43 on elongate flexible arms 33 and is provided with holes therein to expose the electrodes to the outside of elongate flexible arms 33.

Cylindrical mounting structure 21 is disposed between distal extremity 28 of flexible elongate tubular member 23 and basket assembly 32. Cylindrical mounting structure 21 is mounted to and carried by distal extremity 28 and assists in interconnecting basket assembly 32 to flexible elongate tubular member 23 as illustrated in FIGS. 1 through 3. A longitudinally-extending cylindrical mandrel 62 made of a suitable material such as ceramic and having proximal and distal end portions 62a and 62b and a central portion 62c is included as part of cylindrical mounting structure 21. Mandrel 62 is provided with an axially-extending central bore 63 extending longitudinally through proximal and distal end portions 62a and 62b and has a segmented outer surface 67 so as to be octagonal in cross-section as shown in FIG. 4. At least one rectangular shaped and longitudinally-extending cavity 68 is formed in and opens through segmented outer surface 67. In FIGS. 3 and 4, three rectangular shaped and longitudinally-extending cavities 68 are formed in outer surface 67 and are peripherally or circumferentially spaced-apart thereabout. A radially-extending bore or port 69 connects each cavity 68 to central bore 63. Mandrel 62 is formed with first or proximal and second or distal annular recesses 71 and 72 at respective proximal and distal end portions 62a and 62b thereof. Recesses 71 and 72 are formed in outer surface 67 and extend to respective opposite ends of mandrel 62.

Cylindrical mounting structure 21 includes a flex circuit 75 formed from a flexible member or strip 76 made of a suitable plastic such as polyimide having a thickness ranging from 0.0010 to 0.0015 inches. Flexible sheet or strip 76 is generally rectangular in shape when viewed in plan as in FIG. 6 and has proximal and distal end portions 76a and 76b and a central portion 76c. An elongate strip or tail portion extends longitudinally from proximal end portion 76a. Flexible strip 76 has opposite generally parallel first or inner and second or outer surfaces 77 and 78, and is formed with opposite generally parallel first and second longitudinally-extending edges 81 and 82. A longitudinally-extending strip of a suitable metal such as copper foil 83 is disposed on outer surface 78 adjacent each edge 81 and 82.

Flexible strip 76 is slitted with a knife or die (not shown) to provide parallel spaced-apart slits 87 extending longitudinally along proximal and distal end portions 76a and 76b for forming a plurality of eight spaced-apart tabs 88 thereon (See FIG. 6). An equal number of slits 87 are provided on proximal and distal end portions 76a and 76b and corresponding pairs of slits are generally colinear. Accordingly, an equal number of longitudinally-aligned tabs 88, each having a width of approximately 0.040 inches, is formed in each end portion 76a and 76b of flexible strip 76.

Flexible strip 76 is sized and configured for mounting at least one longitudinally-extending semiconductor device on central portion 76c thereof. In FIG. 6, three semiconductor devices are shown mounted in spaced-apart positions across central portion 76c. A lead pattern 87 is carried by flexible strip 76 for permitting access to the semiconductor devices when they are mounted on the flexible strip. Lead pattern 91 is formed on inner surface 77 from a layer of a suitable conductive material such as copper disposed thereon by either additive or subtractive techniques known to those skilled in the art. Lead pattern 91 includes a plurality of contact pads 92 formed in central portion 76c of flexible strip 76. Contact pads 92 are grouped into three closely-arranged patterns.

Lead pattern 91 further includes a plurality of first interconnect pads 96 formed in a pattern on each tab 88 of distal end portion 76b and a plurality of second interconnect pads 97 formed in a pattern on each tab 88 of proximal end portion 76a. First and second interconnect pads 96 and 97 serve as longitudinally spaced-apart first and second interconnect pad means of flex circuit 75. Additional interconnect pad means in the form of interconnect pads 98 is provided on the proximal end of extension or tail portion 76d of flexible strip 76. For simplicity, only a representative portion of lead pattern 91 is shown in FIG. 6.

The pattern of first and second interconnect pads 96 and 97 on tabs 88 is substantially the same as the pattern of first and second interconnect pads 57 and 58 formed on first and second proximal strip portions 51a and 52a, respectively. Flex circuit 75 has a number of contact pads 92 and a number of interconnect pads 96 and 97 in each instance at least equal to the number of electrodes 42 and 43 on basket assembly 32. Lead pattern 91 includes a plurality of leads 99 which serve as conductor means to electrically connect contact pads 92 with first and second interconnect pads 96 and 97 disposed nearby on flex circuit 75 and additional leads 100 which serve as conductor means to electrically connect contact pads 92 with interconnect pads 98 on tail portion 76d.

Figure 8:
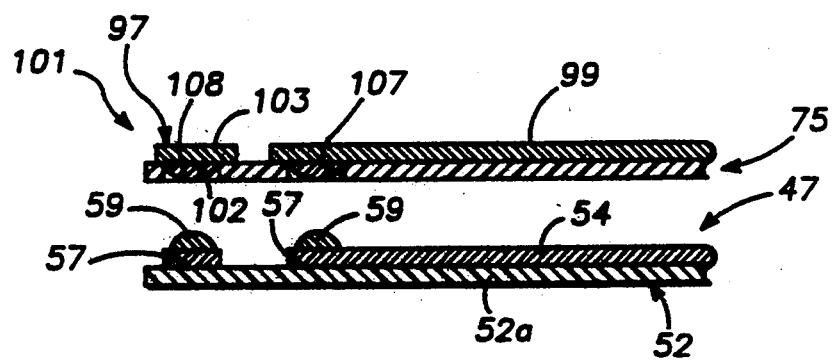
FIG. 8 is a cross-sectional view, prior to assembly, taken along the line 8—8 of FIG. 6.

First and second interconnect pads 96 and 97 face outwardly from outer surface 78 of flexible strip 76. In this regard, each tab 88, together with respective first interconnect pads 96 or second interconnect pads 97 thereon, form part of an interconnect pad structure 101 which is illustrated in FIG. 8 with respect to a tab 88 of proximal end portion 76a having second interconnect pads 97 disposed thereon. Flexible strip 76 serves as a layer of insulating flexible material for structure 101 with inner surface 77 serving as the first side thereof and outer surface 78 serving as the second side thereof. Each generally planar second interconnect pad 97 disposed on inner surface 77 of tab 88 serves as a conductive element and has a first surface 102 facing inner surface 77 and an opposite second surface 103. Portions of flexible strip 76 have been relieved, etched or otherwise removed in a manner known to those skilled in the art to provide a hole or via 107 extending from first surface 102 of each interconnect pad 97 through inner and outer surfaces 77 and 78. Vias 107 do not extend through first interconnect pads 97 and, as a result, the inner portion of each first interconnect pad exposed by a via serves as a generally planar interconnect pad facing outwardly and away from outer surface 78 of flexible strip 76. In this manner, vias 107 permit access to first interconnect pads 97 from outer surface 78. The exposed portion of each first surface 102 has a solder bump 108 formed thereon. Generally circular first and second interconnect pads 96 and 97 have a diameter of approximately 0.020 inches and a thickness of approximately 0.0005 inches. Each via 107 has a generally circular cross-section with a diameter of approximately 0.010 inches.

At least one semiconductor device or chip 111 is mounted to inner surface 77 of flexible strip 76. In FIGS. 3 and 4, three semiconductor chips 111 are shown mounted to inner surface 77 of flexible strip 76 in spaced-apart positions which correspond in spaced-apart relationship to the peripheral positions of cavities 68 formed in segmented outer surface 67 of mandrel 62. Elongate and generally rectangular semiconductor chips 111 are each flip chips having a first surface 112 provided with a plurality of contact terminals 113 formed thereon in a pattern corresponding to one of the patterns of contact pads 92 of flex circuit 75 (See FIGS. 6 and 7). Solder bumps 117 are provided on contact terminals 113 and serve as means for bonding and electrically connecting the contact terminals to contact pads 92 of lead pattern 91 and for mounting semiconductor chips 111 to inner surface 77 of flexible strip 76. Semiconductor chips 111 include multiplexers for combining the electrical signals obtained by electrodes 42 and 43 onto a single waveform. Lead pattern 91 includes additional leads 118 having contact pads at each end thereof and serving to electrically connect semiconductor chips 111 so as to permit communication therebetween. It should be appreciated that semiconductor devices other than flip chips and having conventional contact terminals with leads bonded thereto can be used in apparatus 22 and be within the scope of the present invention.

Figure 9:
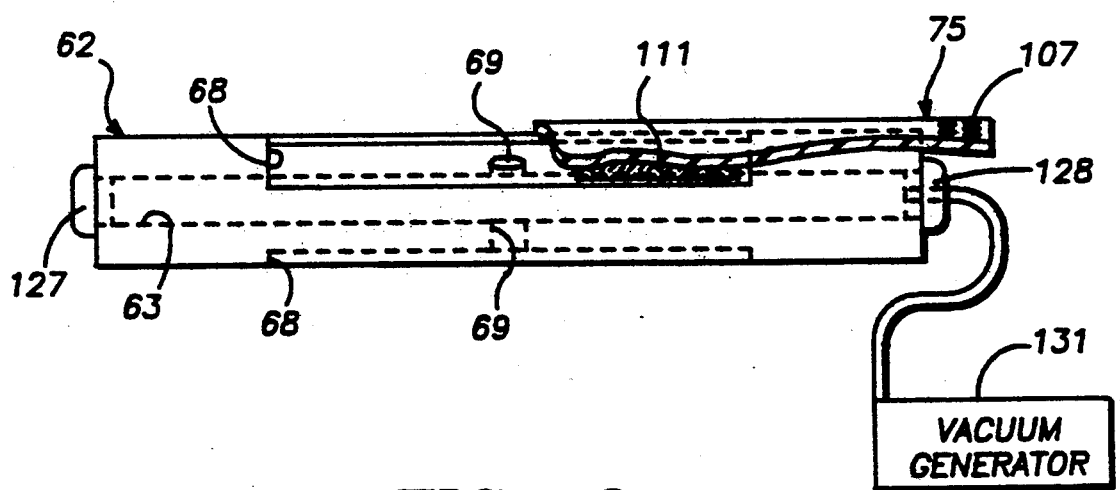
FIG. 9 is a side elevational view of a portion of the method for assembling the cylindrical mounting structure of the present invention.

The method for mounting flex circuit 75 to mandrel 62 to form cylindrical mounting structure 21 for use at distal extremity 28 of apparatus 22 is shown generally in FIG. 9 and can now be described. In general, flex circuit 75 is wrapped around mandrel 62 with flexible strip 76 and semiconductor chips 111 are attached to the mandrel within each cavity 68 so as to permit proper positioning of the flexible strip on the mandrel and permanent attachment thereto. More specifically, the ends of central bore 63 in mandrel 62 are plugged by first and second plugs 126 and 127 and a vacuum generator 131 attached to second plug 127 so as to create a negative pressure or vacuum within the central bore. Vacuum ports 69 cause a negative pressure to also exist in each of cavities 68. Thereafter, flex circuit 75 is folded around segmented outer surface 67 of mandrel 62, with each semiconductor chip 111 being sequentially placed within a corresponding cavity 68 of the mandrel and longitudinally aligned tabs 88 on opposite proximal and distal end portions 76a and 76b being aligned on a segment of outer surface 67. The negative pressure in cavities 68 serves to retain semiconductor chips 111 within the cavities and exert an inwardly directed force on inner surface 77 of flexible strip 76. In this manner, relative movement between flex circuit 75 and mandrel 62 is limited or restricted while first and second edges 81 and 82 of the flexible strip are positioned so as to generally abut each other and respective foil strips 83 thereon are placed in juxtaposition with each other. A bead of solder 132 is disposed on foil strips 83 along edges 81 and 82 for connecting and securing the edges together and securing flex circuit 75 to mandrel 62.

Flexible strip 76 can be described as a longitudinally-extending hollow flexible tubular member when edges 81 and 82 thereof are so connected by solder 132. As so configured, tubular flexible strip 76 is concentrically mounted to mandrel 62 and has a plurality of longitudinally spaced-apart first and second interconnect pads 96 and 97. First interconnect pads 96 are peripherally or circumferentially spaced-apart along distal end portion 76b of flexible strip 76 on tabs 88 thereof and second interconnect pads 97 are peripherally or circumferentially spaced-apart along proximal end portion 76a of the flexible strip on tabs 88 thereof. The exposed portions of first surfaces 102 of first and second interconnect pads 96 and 97 face outwardly and away from outer surface 78 of flexible strip 76 so as to permit first and second leads 53 and 54 to be electrically connected thereto. Semiconductor chips 111 are mounted to the inside of flexible strip 76 and are radially and circumferentially spaced apart. Cylindrical mounting structure 21 and flex circuit 75 thereof have a length ranging from 0.10 to 0.75 inches and preferably 0.30 to 0.50 inches and a transverse dimension ranging from 0.07 to 0.12 inches.

After assembly of cylindrical mounting structure 21, basket assembly 32 is mounted to distal end portion 62b of mandrel 62 and distal end portion 76b of flexible strip 76. In this regard, metal ring 41 with metal strips 40 of elongate flexible arms 33 joined thereto is pressed into distal annular recess 72 and further secured to mandrel 62 by any suitable means such as an adhesive. First leads 53 of each elongate flexible arm 33 are electrically connected to an interconnect pad structure 101 which includes a tab 88 and first interconnect pads 97 as discussed above. Second leads 54 of each elongate flexible arm 33 are electrically connected to an interconnect pad structure 101 which includes a tab 88 and second interconnect pads 97. A separate first interconnect pad 96 is provided for each first electrode 42 and corresponding first lead 43 and first interconnect pad 57 of basket assembly 32 and a separate second interconnect pad 97 is provided for each second electrode 43 and corresponding second lead 54 and second interconnect pad 58 of the basket assembly. Solder bumps 59 and 108 serve as means for electrically connecting and bonding first interconnect pads 57 to first interconnect pads 96 and second interconnect pads 58 to second interconnect pads 97 and are also included within the means for electrically connecting first leads 53 to first interconnect pads 57 of flex circuit 75 and for electrically connecting second leads 54 to second interconnect pads 58 of the flex circuit. Leads 100, connected to interconnect pads 57 and 58, permit electrical connections between leads 53 and 54 from basket assembly 32 and semiconductor chips 111.

The method for connecting first and second flex circuits 46 and 47 to flex circuit 75 can be briefly described as follows. First and second proximal strip portions 51a and 52a are placed against outer surface 78 of the corresponding tab 88 in a position so that corresponding first interconnect pads 57 and 96 are aligned and corresponding second interconnect pads 58 and 97 are aligned. When flex circuits 46 and 47 and flex circuit 75 are so positioned, corresponding solder bumps 59 and 108 are in general engagement with each other. Heat is applied to each pair of aligned tabs 88 and respective proximal strip portions 51a and 52a so as to cause solder bumps 59 and 108 to liquify and bond. As can be appreciated by those skilled in the art, the polyimide forming first and second strips 51 and 52 and flexible strip 76 has a melting point of approximately 400° C. so as to permit sufficient heating of solder bumps 59 and 108 without damage to the polyimide strips.

First and second flex circuits 46 and 47 are sized and configured so that when so mounted to flex circuit 75, first strip portions 51a and first interconnect pads 57 thereon overlie first interconnect pads 96 on flexible strip 76 and second strip portions 52a extend across outer surface 78 of flexible strip 76 so that second interconnect pads 58 thereon overlie second interconnect pads 97 of the flexible strip (See FIGS. 2, 3 and 7). It should be appreciated, however, that proximal strip portions 51a of first flex circuits 46 could have interconnect pad structures thereon similar to interconnect pad structures 101 so as to permit the first flex circuits to be mounted on inner surface 77 of flexible strip 76 and be within the scope of the present invention. In that case, first interconnect pads 57 of first flex circuits 46 would interconnect to second surfaces 103 of first interconnect pads 96 on flex circuit 75. Accordingly, at least one of first and second interconnect pads 96 and 97 and more specifically second interconnect pads 97 at proximal end portions 76a of flexible strip 76 face outwardly from outer surface 78 of the flexible strip.

Cylindrical mounting structure 21, with basket assembly 32 so mounted thereto, is secured to distal extremity 28 of flexible elongate tubular member 23. Distal extremity 28 is formed with a sleeve 136 which extends over proximal annular recess 71 of mandrel 62 and is further secured thereto by any suitable means such as an adhesive. Sleeve 136 and proximal annular recess 71 are included within the cooperative mating means for securing cylindrical mounting structure 21 to flexible elongate tubular member 23.

At least one conductor element or wire 140 extends longitudinally through lumen 31 of flexible elongate tubular member 23 and is electrically connected to an interconnect pad 98 on flex circuit 75 so as to permit transmission of the multiplexed waveform from semiconductor chips 111 to proximal extremity 27 of the flexible elongate tubular member (See FIG. 3). Flexible elongate tubular member 23 is provided with a hole or port 141 which extends through the outer surface thereof into lumen 31. Tail portion 76d extends along the outer surface of flexible elongate tubular member 23 and into port 141 and lumen 31 so that interconnect pads 98 carried by the end thereof are disposed in lumen 31. Wire 140 is bonded to the appropriate interconnect pad 98 by a suitable means such as solder 142 which serves as means for electrically connecting wire 140 to interconnect pad 98. The lead 100 which carries the multiplexed waveform includes a bus, not shown in the drawings, for electrically connecting the interconnect pad 98 to each of semiconductor chips 111. Additional wires 143 extend longitudinally through lumen 31 and are similarly connected to interconnect pads 98 of cylindrical mounting structure 21 so as to permit, among other things, the supply of ground, power and logic signals to the cylindrical mounting structure and basket assembly 32.

Cylindrical mounting structure 21 is further secured to distal extremity 28 of flexible elongate tubular member 23 by a flexible sleeve or tube 147 made of a suitable material such as plastic which is slipped over cylindrical mounting structure 21 and distal extremity 28 and shrunk thereto by means of heat. When basket assembly 32 is so mounted to flexible elongate tubular member 23, first and second leads 53 and 54 of each elongate flexible arm 33 extend to distal extremity 28 and into flexible elongate tubular member 23 for conducting electrical energy from first and second electrodes 42 and 43 to the flexible elongate tubular member. Cylindrical mounting structure 21 has electrical means or apparatus, which is electrically connected to first and second leads 53 and 54 and includes semiconductor chips 111 and flex circuit 75, for performing electrical functions with respect to first and second electrodes 42 and 43. Semiconductor chips 111 are carried by distal extremity 28 of flexible elongate tubular member 23 in close proximity to basket assembly 32.

It should be appreciated that a plurality of cylindrical mounting structures 21 can be provided on a medical apparatus and be within the scope of the present invention. For example, several cylindrical mounting structures 21 could be provided in spaced-apart position at the distal extremity or end of the flexible elongate tubular member adjacent the basket assembly for accommodating more electrode leads than can be handled by only one cylindrical mounting structure. In another example, a first cylindrical mounting structure could be provided at the end of the flexible elongate tubular member for serving the electrodes on the proximal portion of the basket assembly and a second cylindrical mounting structure could be provided at the tip of the basket assembly for serving the electrodes on the distal portion of the basket assembly.

Medical apparatus 22 can further include a secondary steerable ablation catheter 151 of the type described in copending application Ser. No. 07/894,529 filed Jun. 5, 1992, now U.S. Pat. No. 5,324,284. Steerable catheter 151 extends through a central lumen 152 provided in flexible elongate tubular member 23 and central bore 63 of mandrel 62 as illustrated in FIGS. 2 through 5. Wire 140 extends through proximal extremity 27 of flexible elongate tubular member 23 and is electrically connected to a computer 156 with a video monitor 157. Computer 156 demultiplexes the waveform containing the signals detected by first and second electrodes 42 and 43 and displays them on video monitor 157. Wires 143 are electrically connected to computer 156 and a power supply and control console 158 for controlling basket assembly 32 and steerable catheter 151.

In operation and use, basket assembly 32 and steerable catheter 151 of medical apparatus 22 can be introduced into a ventricle of a heart and operated in substantially the same manner as discussed in copending applications Ser. No. 07/919,198 filed Jul. 24, 1992, now U.S. Pat. No. 5,279,299, and Ser. No. 07/894,529 filed Jun. 5, 1992, now U.S. Pat. No. 5,324,284. Once positioned within the chamber of the heart, basket assembly 32 is moved from its contracted position to its expanded position and first and second electrodes 42 and 43 are moved into engagement with the wall forming the chamber of the heart for detecting electrical energy therefrom.

In view of the foregoing, it can be seen that a new and improved endocardial mapping apparatus which utilizes a significant number of electrodes has been provided. The apparatus includes a semiconductor device with multiplexers provided on the distal extremity thereof. The semiconductor device is carried by a cylindrical mounting structure with interconnect pads spaced around the proximal and distal end portions thereof. The cylindrical mounting structure utilizes a flex circuit having an interconnect pad on one side thereof which is electrically accessible from the other side without the necessity of an electroplated feedthrough hole. The invention includes a method by which a flex circuit is initially secured by negative pressure to a mandrel while forming the cylindrical mounting structure.

What is claimed is:

1. Apparatus for mapping a wall of a chamber of a heart comprising a flexible elongate tubular member having proximal and distal extremities and being provided with at least one lumen extending therethrough, a plurality of longitudinally and radially spaced-apart electrodes, expandable means carried by the distal extremity of the flexible elongate tubular member and being movable between a contracted position and an expanded position, means mounting the electrodes on the expandable means whereby when the expandable means is moved to the expanded position in the chamber of the heart the electrodes are moved into engagement with the wall forming the chamber of the heart, lead means for conducting electrical energy in contact with the electrodes and extending into the flexible elongate tubular member and electrical means connected to the lead means for performing electrical functions with respect to the electrodes, the electrical means including at least one semiconductor device carried by the distal extremity of the flexible elongate tubular member in close proximity to the expandable means.

2. Apparatus as in claim 1 wherein at least twenty electrodes are mounted on said expandable means.

3. Apparatus as in claim 1 wherein said electrical means includes at least two circumferentially spaced-apart semiconductor devices carried by the distal extremity of the flexible elongate tubular member in close proximity to the expandable means.

4. Apparatus as in claim 3 wherein said semiconductor devices include multiplexers.

5. Apparatus as in claim 3 further comprising a longitudinally-extending mandrel carried by said distal extremity and having an outer surface with peripherally spaced-apart cavities formed therein and a longitudinally-extending hollow flexible member concentrically mounted on the mandrel and having an inside, the semiconductor devices being mounted on the inside of the hollow flexible member and disposed in the cavities of the mandrel and conductor means carried by the hollow flexible member for electrically connecting the lead means and the semiconductor devices.

6. Apparatus as in claim 5 wherein said semiconductor devices have contact terminals and wherein solder bumps are formed on the contact terminals and serve to bond the contact terminals to said conductor means carried by the hollow flexible member.

7. Apparatus for mapping a wall of a chamber of a heart comprising a flexible elongate tubular member having proximal and distal extremities and at least one lumen extending therethrough, a basket assembly carried by the distal extremity of the flexible elongate tubular member and being movable between contracted and expanded positions, the basket assembly having a plurality of elongate flexible circumferentially spaced-apart arms with proximal and distal extremities and a plurality of longitudinally spaced-apart first and second electrodes carried by each arm for engaging the wall of the heart, first and second lead means connected to respective first and second electrodes of each arm for conducting electrical energy in contact with the electrodes to the proximal extremities of the arms, a longitudinally-extending hollow flexible member carried by the distal extremity of the flexible elongate tubular member, at least one semiconductor device mounted on the hollow flexible member, the hollow flexible member having a plurality of longitudinally spaced-apart first and second interconnect pads electrically connected to the semiconductor device, and means for electrically connecting the first lead means to the first interconnect pads and for electrically connecting the second lead means to the second interconnect pads.

8. Apparatus as in claim 7 wherein said hollow flexible member has a length ranging from 0.10 to 0.75 inches and a transverse dimension ranging from 0.07 to 0.12 inches.

9. Apparatus as in claim 7 wherein said hollow flexible member has proximal and distal end portions and wherein said first interconnect pads are circumferentially spaced apart around the distal end portion and the second interconnect pads are circumferentially spaced apart around the proximal end portion.

10. Apparatus as in claim 9 wherein said hollow flexible member has an outer surface with said first and second interconnect pads facing outwardly therefrom and wherein said arms include first and second strip portions for carrying said first and second lead means, the first strip portions overlying the first interconnect pads and the second strip portions extending across the outer surface of the hollow flexible member and overlying the second interconnect pads.

11. Apparatus as in claim 10 together with a longitudinally-extending mandrel having an outer surface with a cavity formed therein, wherein said hollow flexible member has an inside and wherein said semiconductor device is mounted on the inside of said hollow flexible member and said hollow flexible member is concentrically mounted on the mandrel with the semiconductor device disposed in the cavity.

12. Apparatus as in claim 7 together with at least one conductor element extending longitudinally through said flexible elongate tubular member and wherein said hollow flexible member has a proximal end portion with a tail portion extending longitudinally therefrom, the tail portion being provided with an additional interconnect pad, and means for electrically connecting the conductor element to the additional interconnect pad.

13. A cylindrical mounting structure for use with a medical apparatus having a flexible elongate tubular member with a distal extremity for insertion into a vessel in a body and a probe device having first and second lead means for conducting electrical energy, the cylindrical mounting structure comprising a mandrel having a segmented outer surface with at least one cavity opening through the segmented outer surface, means for coupling the mandrel to the distal extremity of the flexible elongate tubular member and to the probe device carried by the mandrel and adapted to couple the mandrel to the distal extremity of the flexible elongate tubular member and to the probe device, a flex circuit wrapped about the segmented outer surface of the mandrel and having an inner surface provided with contact pads thereon, at least one semiconductor device mounted on the inner surface of the flex circuit and disposed in the cavity, the semiconductor device having contact terminals in electrical contact with the contact pads on the flex circuit, the flex circuit having longitudinally spaced-apart first and second interconnect pads adapted for electrical connection to the respective first and second lead means and conductor means for electrically connecting the first and second interconnect pads to the contact pads.

14. Apparatus as in claim 13 wherein said flex circuit has an outer surface opposite to said inner surface and wherein at least one of said first and second interconnect pads has a surface which faces outwardly from said outer surface.

15. Apparatus as in claim 13 wherein said flex circuit has an outer surface opposite to said inner surface and has opposite generally parallel first and second longitudinally-extending edges, strips of metal disposed on the outer surface adjacent each edge and a bead of solder disposed on the strips of metal along the edges for connecting the edges together.

* * * * *